United States Patent
Warner et al.

(10) Patent No.: US 6,765,110 B2
(45) Date of Patent: Jul. 20, 2004

(54) PROCESS FOR THE SIMULTANEOUS COPRODUCTION AND PURIFICATION OF ETHYL ACETATE AND ISOPROPYL ACETATE

(75) Inventors: R. Jay Warner, Corpus Christi, TX (US); Carl David Murphy, Corpus Christi, TX (US); Gustavo Angel Robelo Grajales, Veracruz (MX); Francisco Javier Sanchez Santiago, Veracruz (MX); Fernando Alejo Solorzano, Veracruz (MX); Jose Alfonso Torres, Corpus Christi, TX (US)

(73) Assignee: Celanese International Corporation, Dallas, TX (US)

(*) Notice: Subject to any disclaimer, the term of this patent is extended or adjusted under 35 U.S.C. 154(b) by 587 days.

(21) Appl. No.: 09/740,224

(22) Filed: Dec. 19, 2000

(65) Prior Publication Data

US 2003/0166964 A1 Sep. 4, 2003

(51) Int. Cl.[7] .......................... C07C 67/03; C07C 67/54
(52) U.S. Cl. ..................................... 560/265; 560/248
(58) Field of Search ................................. 560/248, 265

(56) References Cited

U.S. PATENT DOCUMENTS

| 3,898,291 A | 8/1975 | Darsi et al. ............. 260/643 D |
| 4,710,274 A | 12/1987 | Berg et al. ..................... 203/51 |
| 4,826,576 A | * 5/1989 | Berg et al. ..................... 203/56 |

FOREIGN PATENT DOCUMENTS

| WO | WO 98/25876 | 6/1998 |
| WO | WO 98/426952 | 10/1998 |

OTHER PUBLICATIONS

Simons, R. M., "Esterification" in Encyclopedia of Chemical Process and Design vol. 19, J. J. McKetta (ed.), p. 384, Marcel Dekker, Inc., 1983.

* cited by examiner

Primary Examiner—Peter O'Sullivan
(74) Attorney, Agent, or Firm—M. Susan Spiering

(57) ABSTRACT

This invention relates to a process for the simultaneous coproduction of ethyl acetate and isopropyl acetate. The esterification reaction comprises contacting acetic acid with a mixed alcohol stream of ethanol and isopropanol. Exemplified is a purified, Fischer Tropsch derived mixture of ethanol and isopropanol. The esterification reaction occurs in the presence of an acidic catalyst in a liquid phase reaction system. The resultant crude reaction step product is separated and purified by distillation to produce acetate ester products having greater than 99.5 wt % purity.

9 Claims, 1 Drawing Sheet

Co-Production of Ethyl and isoPropyl Acetates

PROCESS FOR THE SIMULTANEOUS COPRODUCTION AND PURIFICATION OF ETHYL ACETATE AND ISOPROPYL ACETATE

FIELD OF THE INVENTION

This invention relates to the production of organic carboxylic acid esters and in particular to a process for simultaneously coproducing ethyl acetate and isopropyl acetate in a reaction mixture comprising a mixed alcohol stream of ethanol and isopropanol, with acetic acid, in the liquid phase in the presence of an acidic catalyst. The invention further relates to the subsequent separation of ethyl acetate and isopropyl acetate from the crude acetate ester mixture, and to the removal of impurities which may be present.

BACKGROUND

It is well known to produce esters such as ethyl acetate or isopropyl acetate by reaction of an ethanol or isopropanol respectively with acetic acid in the presence of an acidic catalyst. However, in the coproduction of esters, difficulty is encountered in driving the esterification reactions to completion, especially with mixtures of alcohols with dissimilar reactivity, thereby resulting in acetate product contaminated with unreacted alcohols. It is also known to coproduce these esters in a single reactor by operating the reactor sequentially, i.e., by first producing one ester by reaction of the acid with the first alcohol, and then in a swing operation changing over to a second alcohol to produce the second ester. In all of these reactions involving the use of a mixture of alcohols for esterification, it is important to use relatively pure reactants for reaction with acetic acid. This is especially important if the esters are coproduced in a process for the simultaneous rather than the sequential production of both esters. The use of reactants of high purity may not be economic commercially for it would add significantly to the cost of producing both esters. It has been relatively difficult to coproduce simultaneously a mixture of these esters from a relatively impure set of reactants, primarily because if the alcohol is contaminated with impurities, for example, "heavy" or $C_3$ or greater alcohols, it is difficult to separate the eventual ester product from the impurities.

WO 98/42652 (BP Chem.) describes ester coproduction for the coproduction of ethyl acetate and n-butyl acetate. The reference describes use of impure crude industrial ethanol and "oxo" based n-butanol in a liquid phase esterification reaction system. The process is capable of using relatively impure reactants and provides for removing some of the aldehyde type impurities of the alcohols by the use of resin guard beds.

WO 98/25876 (Sasol Chem.) describes production of organic carboxylic acid esters employing Fischer Tropsch derived alcohols or carboxylic acids, said esterfication reaction occurring in the vapor phase. Among other esters, WO'876 exemplifies the production of ethyl acetate and/or butyl acetate. It is stated that due to the complexity of Fischer Tropsch product streams, it is normally uneconomic to purify the alcohols obtained to a purity in excess of 99%. WO '876 describes use of the Fischer Tropsch alcohol without purification prior to use. The alcohol, or Fischer Tropsch carboxylic acid, if used, is employed as is and blended with acetic acid in the reaction system.

SUMMARY

The present invention is directed to a process for the simultaneous coproduction of ethyl acetate and isopropyl acetate, comprising reacting an alcohol mixture of ethanol and isopropanol with acetic acid, in the liquid phase, in the presence of an acidic catalyst wherein the reaction is carried out at elevated temperature and at a pressure sufficient to effect esterification of the reactant. An example of an alcohol mixture is that which is derived from the purification of a Fischer Tropsch alcohol mixture. Fischer Tropsch alcohol mixtures contain impurities. In the present invention, impurities of primary concern are the heavy components, or the $C_3$ or $C_4$ alcohol components of the Fischer Tropsch mixture. The Fischer Tropsch mixture may or may not be purified, prior to use. Purification of the Fischer Tropsch mixture can occur employing distillation or alternatively employing extractive distillation with water. If the Fischer Tropsch mixture is used without prior purification, high boiling ester byproducts are produced during the esterification reaction and removed from the reaction product during the purification process of the respective ethyl and isopropyl acetate products. The crude mixed ester product is separated into purified ethyl and isopropyl acetate products via a series of distillation towers.

Examples of percent alcohol mixtures to employ include alcohol mixtures containing between about 90% ethanol:10% isopropanol to between about 10% ethanol:90% isopropanol, or alternatively the mixture is between about 80% ethanol:20% isopropanol to between about 60% ethanol:40% isopropanol.

Employing the current process, both ethyl acetate and isopropyl acetate are recovered at greater than about 99.5% purity and up to or greater than about 99.7%. Presently the industry accepts specification grade ethyl acetate and specification grade isopropyl acetate as being a minimum purity of 99.5%.

DETAILED DESCRIPTION OF THE INVENTION

Figure 1:
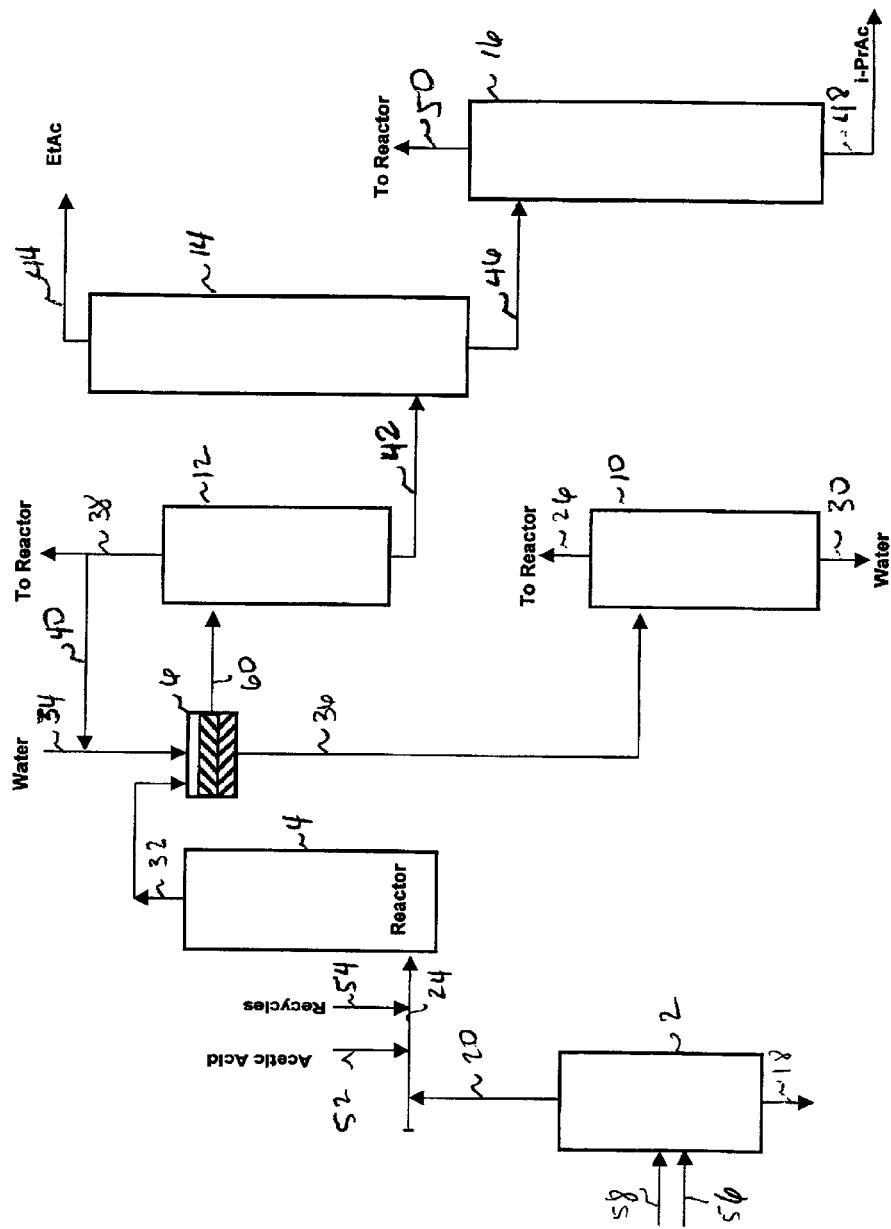
FIG. 1 is a schematic of the ethyl and isopropyl acetate coproduction process.

A continuous coproduction process is illustrated in FIG. 1. A homogeneous or heterogeneous catalyst may be employed in the present esterification reaction. The acid catalyst should be temperature stable at the temperature which the reaction is effected, i.e., does not deteriorate to an appreciable extent at the temperature at which the reaction is effected. The acid catalyst may comprise any conventional esterification catalyst. It is preferred that sulfonic acids or ion exchange resins with strongly acidic functionalities be employed.

The temperature at which the reaction is effected is determined by the steady state composition and operating pressure of the liquid phase catalyzed reaction zone, being typically in the range of 90 to 150° C.

Suitable pressure for the present invention is from about 1 to 3 atmospheres. Present binary and tertiary azeotropes are slightly pressure sensitive so reaction pressure is selected based primarily on operating parameters such as throughput, energy consumption, and corrosion.

It is preferred that an excess concentration of acid be present in the liquid phase catalyzed reaction zone to preferentially drive the esterification, and to minimize hydrolysis of etherification reactions, thus increasing conversion and selectivity towards the desired products. In general, the acetic acid concentration in the reaction zone ranges from about 50 to 80 wt %, most preferably between about 60 and 70 wt %.

Although the present description is directed to separation of acetate esters, there is a body of information dealing with separation of alcohols, for example U.S. Pat. No. 4,710,274, U.S. Pat. No. 3,898,291. It was found that for producing the desired acetate esters (ethyl acetate/isopropyl acetate), the preferred route was to coproduce the acetate esters and separate them at the end of the production process, as opposed to separating the alcohols at the beginning of the process and producing the acetate esters individually.

An embodiment of the present invention is now disclosed. Referring to FIG. 1, a Fischer Tropsch alcohol derived mixture 58 is fed to an alcohol purification column 2. The alcohol mixture comprises ethanol, isopropanol, and small amounts of impurities. Water 56 is also added to column 2 along with the alcohol mixture to assist in the removal of the heavy alcohols. The azeotropic mixture ethanol/isopropanol/water is distilled overhead and directed to reactor column 4. Overhead 20 contains approximately 300 ppm of impurities. The residue of column 2, stream 18, contains primarily water and $C_3$ and $C_4$ alcohol heavies as impurities. The removal of $C_3$ alcohol (n-propanol) in the alcohol purification column 2 is desired in the coproduction of ethyl acetate and isopropyl acetate since residual n-propanol, if present in the desired mixed alcohol stream will react with acetic acid to form n-propyl acetate. The presence of n-propyl acetate in the final isopropyl acetate product can be removed with a heavy ends purification column. Heavy ends alcohols are defined as having a higher boiling point than n propyl alcohol or ethanol. These high boiling alcohols generate high boiling or heavy end esters. Although n propyl acetate can be separated from isopropyl acetate, the removal of n propyl alcohol from the mixed alcohol feed precludes the need for separation of the heavy acetate (n propyl acetate) at the end of the purification train. Column 2 operates at about 1.2 bar, with the water addition slightly higher in the column than the feed tray.

Overhead 20, ethanol-isopropanol blend containing less than 300 ppm of heavier alcohol impurities, is condensed and directed as a liquid to the reactor column 4 and contacted with acetic acid 52, an acid catalyst, plus recycles 54 (which will be discussed hereinbelow). An alternate embodiment to employing purified Fischer Tropsch mixed alcohol stream, and not shown in FIG. 1, is to feed a mixed alcohol stream to reactor 4. The mixed alcohol stream may contain impurities or be free thereof. Impurities will cause byproduct formation which can be processed at the end of the purification train. Examples of impurities most likely to be formed when using impure alcohol mixtures include high boiling esters such as n-propyl acetate and sec butyl acetate. Those of skill in the art will recognize that conventional techniques may be employed to remove the byproduct formations. For example, a column may be added after the isopropyl acetate light ends removal column 16 to remove such impurities as a heavy ends purge.

In the reactor 4, water is formed during the esterification reaction. It is desired to azeotrope this water out of the reaction zone as to favor the esterification and to minimize the hydrolysis of the ethyl and isopropyl acetates back to alcohol and acetic acid. To accomplish that a crude liquid ester mixture, 50, is recycled to the reactor 4. In general, the acetic acid concentration in the base of column 4 ranges from about 50 to 80 wt %, most preferably between about 60 and 70 wt %. Lower acid concentrations would decrease alcohol conversion making the purification of the esters more difficult to achieve. Reactor column 4 operates in the liquid phase, under the general conditions of about 90–150° C. and about 1 to 3 atmospheres.

Overhead 32 containing a crude mixture of ethyl/isopropyl acetate reaction product plus water produced by the esterification reaction, and small amount of unreacted alcohols, is condensed and directed to decanter 6 which serves to separate the organic and aqueous layers of the reaction product mixture. The composition of stream 32 is dictated by the ratio of ethanol/isopropanol fed to the reactor, alcohol conversion, and the binary and tertiary azeotropes present in the system. The organic phase, stream 60, comprises primarily ester and isopropyl acetate and smaller amounts of alcohols and water. The aqueous phase, stream 36, contains about 90–95% water and the remaining is alcohols and acetates.

Water is optionally added to decanter 6 via stream 34, which is admixed with overhead 32, and serves as an extractive agent in the decantation or separation process. The water takes some alcohols from the organic into the aqueous phase thus making the operation of column 12 easier. Water stream 34 maybe recycled water from residue 30 of the alcohol recovery column 10 or may be a fresh, relatively pure water source. Decanter 6 operates at a temperature of about 5 to 35° C., preferably between about 10 and 20° C.

Stream 36 is directed, with or without preheating, to column 10, the alcohol recovery column for processing. The acetates and alcohols are stripped from the water to recover basically all organics and leave essentially pure water (containing less than ppm levels of organic components) in the residue. Water 30, can be recycled and utilized as the extractive agent 34 in the separation of the organic and aqueous layer in the overhead decanter of the reactor column. Reaction water found in residue 30 is directed to waste for treatment.

The organic phase, containing most of the ethyl/isopropyl acetate desired products, is recovered and exits decanter 6 as a side stream 60. Typical composition of stream 60 is approximately 94% total (i.e., ethyl and isopropyl) acetates with the remainder being water and unreacted alcohols.

Stream 60 is directed to the alcohol stripping column 12 which serves to strip the water and unreacted alcohols, from the desired ethyl/isopropyl acetate esters. Not shown in FIG. 1, the overhead vapors of column 12, like the overhead vapors of reactor column 4, are first condensed, then mixed with optional extraction water, and finally directed to a second decanter where two phases are formed. At least a portion of the organic phase from the second decanter (stream 38) is recycled to reactor column 4 to prevent alcohols from building-up in the unit, and to remove azetropes from the esterification reaction. Stream 38 contains primarily ethyl acetate with smaller amounts of isopropyl acetate, water, and unreacted alcohols. A portion of stream 38 is directed to the first decanter 6 to recover the approximately 90 wt % acetate esters that the stream contains.

Column 12 operates at about 1 to 3 atmospheres pressure and the base temperature is determined by the boiling point of the mixed esters, e.g. 105° C. at 2 atmospheres. The desired ester product mixture exits the alcohol stripping column 12 as residue 42.

Residue 42 from column 12 contains less than about 200 ppm alcohols and is directed to column 14 which is the ethyl acetate finishing column. Essentially pure (greater than about 99.7 wt % containing less than about 1000 ppm isopropyl acetate) ethyl acetate is separated from the other components as a light ends or low boiling fraction and recovered as a condensed overhead stream 44. Column 14 operates at about 1 to 3 atmospheres.

A mixture of isopropyl acetate and some ethyl acetate is recovered as residue stream 46 from column 14. Stream 46 is directed to column 16 for distillation and purification. Although stream 46 contains some ethyl acetate, it is desirable to minimize ethyl acetate by operation of column 14. Column 16 serves as the isopropyl acetate finishing column. Generally, the flow of the residue 46 into column 16 is adjusted so as the overhead 44 obtains ethyl acetate with less than 1000 ppm of isopropyl acetate. Essentially pure isopropyl acetate (about 99.5 wt %, generally greater than about 99.7 wt % and containing less than about 50 ppm ethyl acetate) is recovered as residue stream 48.

The separation of ethyl and isopropyl acetate requires numerous theoritical plates. Overhead stream 50 contains the ethyl and isopropyl acetates which were not removed during the finishing column process. Stream 50 is condensed and recycled to the reactor to help azeotrope the reaction water out of the liquid phase catalyzed zone. Column 16 operates typically between about 1 and 3 atmospheres.

The overhead stream 50 from isopropyl acetate finishing column 16 is combined with a portion of overhead stream 38 from the alcohol stripping column 12 to form a recycles stream 54 which is directed to the reactor 4 and combined with alcohol and acid for the esterification reaction.

Distillation options for the present invention involve use of one large column, e.g., column 14, as described herein. Alternatively, a combination of several towers to accomplish the distillation may be employed.

EXAMPLES

The present invention was found to yield high alcohol conversions with selectivites to ester products exceeding 97% and at acetic acid reaction zone space time velocities of greater than 5 gmol per liter per hour.

Example 1

A liquid phase reactor was previously charged with 1.5% methane sulfonic acid (MSA) as catalyst. The glass reactor contained 40 trays, 2-inch diameter, and operated at a base temperature of about 100° C.

A reactor feed consisting of acetic acid, and a blend of 83:17% ethanol and isopropanol was used. Since a blend of alcohols was employed, in order to simulate impurities which may be present, the alcohol blend was spiked with n-propanol. The acetic acid to alcohol blend ratio was 1.2 kilo/kilo. The pressure was atmospheric. Feed rates were 5 gr/min of acetic acid, 4.17 gr/min of alcohols blend, and 2.92 gr/min of recycled esters. Steady state conditions were reached.

The reactor was operated continuously for 16 hours during each run. Reactor overhead was condensed at 35° C. and fed to a decanter. The decanter was maintained at 26° C. To the decanter was also fed water to effect and assist separation of the organic and aqueous phase. For the reactor column, three runs were performed (A, B, C) and the run conditions and reactor results are illustrated in Table 1. Runs A, B, and C were identical, except that run C utilized more water addition to the decanter.

From the decanter, the organic phase was directed to the alcohol stripping column. The sample composition employed and conditions and results thereof are found in Table 2.

For these examples, the aqueous phase from the decanter was discarded.

From the alcohol stripping column, the residue was directed to the ethyl acetate finishing tower. The sample composition employed and conditions and results of the ethyl acetate finishing tower are found in Table 3. Ethyl acetate was recovered in 99.96% purity. The residue of the ethyl acetate finishing tower was directed to an isopropyl acetate finishing tower. The sample composition employed and conditions of operation for the isopropyl acetate finishing tower for recovery of isopropyl acetate are found in Table 4. Isopropyl acetate was recovered in 99.95% purity.

For production of <99.95% purity the residue of the isopropyl finishing tower is directed to a heavy ends removal column whereby the heavy ends by byproducts formed during esterification are removed. Conventional techniques known to those of skill in the art are to be employed for the heavy ends removal process.

Abbreviations for the table include OVHD=overhead; HAC=acetic acid; nPaAc=normal propyl acetate; iPrAc=isopropyl acetate; nPrOH=normal propanol; IPA=isopropanol; EtAc=ethyl acetate; EtOH=ethanol; %=wt/wt %.

Example 2

Table 5 illustrates runs containing ethanol/isopropanol ratios of about 60/40 (A) and 10/90 (B) with no impurities added.

A 45 tray reaction tower with thermosiphon reboiler holding about 280 mL of boiling liquid, was electrically heated, and contained a catalyst concentration of about 1% weight methane sulfonic acid. A mixture of esters was added to the reaction zone to azeotrope out this excess water. Overhead vapors were totally condensed and phased in an overhead decanter. Water was added to the decanter to decrease the water concentration in the organic phase relux. Organic phase reflux was pumped to the top tray of the column section. Organic and aqueous phase products were collected and weighed separately. The system operated at atmospheric pressure.

Example 1

TABLE 1

Reactor Column. Conditions and Results

| RUN | | | A | B | C |
|---|---|---|---|---|---|
| Coproduction of Ethyl Acetate and isoPropyl Acetate | | | | | |
| Feed | | % ETOH | 82.570 | 82.570 | 82.570 |
| | | % IPA | 16.820 | 16.820 | 16.820 |
| | | % H2O | 0.250 | 0.250 | 0.250 |
| Organic Phase (OVHD Decanter) | | % HAC | 0.002 | 0.002 | 0.001 |
| | | % H2O | 4.600 | 4.200 | 3.600 |
| | | % ETOH | 1.210 | 1.238 | 0.630 |
| | | % IPA | 0.890 | 0.780 | 0.584 |
| | | % nPROH | 0.005 | 0.004 | 0.002 |
| | | % ETAC | 81.211 | 81.662 | 82.908 |
| | | % iPRAC | 12.000 | 12.050 | 12.200 |
| | | % nPRAC | 0.000 | 0.001 | 0.001 |
| Aqueous Phase (OVHD Decanter) | | % HAC | 0.000 | 0.000 | 0.000 |
| | | % H2O | 94.508 | 95.157 | 94.023 |
| | | % ETOH | 0.980 | 0.850 | 0.705 |
| | | % IPA | 0.760 | 0.600 | 0.485 |
| | | % nPROH | 0.000 | 0.000 | 0.000 |
| | | % ETAC | 3.550 | 3.390 | 4.330 |
| | | % iPRAC | 0.200 | 0.000 | 0.455 |
| | | % nPRAC | 0.000 | 0.000 | 0.000 |
| Liq. Ph. Catalyzed Reaction Zone | | % HAC | 67.486 | 67.486 | 67.486 |
| | | % H2O | 3.000 | 3.000 | 3.000 |
| | | % ETOH | 0.250 | 0.250 | 0.250 |
| | | % IPA | 0.377 | 0.377 | 0.377 |
| | | % nPROH | 0.000 | 0.000 | 0.000 |
| | | % ETAC | 18.830 | 18.830 | 18.830 |
| | | % iPRAC | 9.880 | 9.880 | 9.880 |
| | | % nPRAC | 0.091 | 0.091 | 0.091 |

TABLE 1-continued

Reactor Column. Conditions and Results

| | RUN | A | B | C |
|---|---|---|---|---|
| Main Ratios | | | | |
| Reflux/HAc Feed | K/K | 3.440 | 4.052 | 3.715 |
| Reflux/Distillate | K/K | 1.652 | 1.945 | 1.837 |
| Wash Water/Distillate | K/K | 0.117 | 0.116 | 0.226 |
| Wash Water/HAc Feed | K/K | 0.682 | 0.750 | 1.390 |
| Recycled Esters/HAc Feed | K/K | 1.940 | 1.952 | 1.924 |
| Crude EtAc/Crude iPrAc | K/K | 6.768 | 6.777 | 6.796 |
| Base Temperature | ° C. | 98.8 | 98.9 | 102.7 |
| Top temperature | ° C. | 70.9 | 71.1 | 71.9 |
| Decanter Temperature | ° C. | 28.0 | 26.0 | 24.0 |

Example 1

TABLE 2

Alcohols Striping Column. Conditions and Results

| Wt % | FEED | RESIDUE | DISTILLATE | REFLUX |
|---|---|---|---|---|
| Coproduction of Ethyl Acetate and isoPropyl Acetate | | | | |
| HAC | 0.0053 | 0.0140 | 0.0007 | 0.0007 |
| H2O | 3.3250 | 0.0230 | 5.0600 | 5.0600 |
| ETOH | 1.3605 | 0.0012 | 2.0745 | 2.0745 |
| IPA | 0.9650 | 0.0026 | 1.4705 | 1.4705 |
| NPROH | 0.0009 | 0.0027 | 0.0000 | 0.0000 |
| ETAC | 83.8288 | 80.3939 | 85.6327 | 85.6327 |
| IPRAC | 10.4900 | 19.5350 | 5.7390 | 5.7390 |
| NPRAC | 0.0100 | 0.0230 | 0.0031 | 0.0031 |
| OTHERS | 0.0145 | 0.0046 | 0.0195 | 0.0195 |
| | 100.0000 | 100.0000 | 100.0000 | 100.0000 |
| Ratios | | | | |
| Residue/Feed | K/K | | 0.34 | |
| Reflux/Distillate | K/K | | 0.34 | |
| Top Temperature | ° C. | | 71.1 | |
| Base Temperature | ° C. | | 78.0 | |

Example 1

TABLE 3

Ethyl Acetate Finishing Column. Conditions and Results

| Wt % | Feed | Distillate | Residue |
|---|---|---|---|
| Coproduction of Ethyl Acetate and isoPropyl Acetate | | | |
| HAC | 0.0021 | 0.0011 | 0.0049 |
| H20 | 0.0230 | 0.0252 | 0.0175 |
| ETOH | 0.0043 | 0.0054 | 0.0014 |
| IPA | 0.0032 | 0.0036 | 0.0023 |
| n-PROH | 0.0000 | 0.0000 | 0.0000 |
| ETAC | 80.5539 | 99.9634 | 30.5454 |
| i-PRAC | 19.4070 | 0.0012 | 69.4052 |
| n-PRAC | 0.0062 | 0.0000 | 0.0223 |
| Others | 0.0004 | 0.0001 | 0.0010 |
| | 100.0000 | 100.0000 | 100.0000 |
| Ratios | | | |
| Residue/Feed | K/K | | 0.27 |
| Reflux/Distillate | K/K | | 3.15 |
| Top Temperature | ° C. | | 76.4 |
| Base Temperature | ° C. | | 84.4 |

Example 1

TABLE 4 isoPropyl Acetate Finishing Column. Conditions and Results

| WT % | FEED | RESIDUE | DISTILLATE |
|---|---|---|---|
| Coproduction of Ethyl Acetate and isoPropyl Acetate | | | |
| H2O | 0.0440 | 0.0173 | 0.0635 |
| MC | 0.0028 | 0.0004 | 0.0046 |
| IPA | 0.0029 | 0.0005 | 0.0047 |
| N-PROH | 0.0000 | 0.0000 | 0.0000 |
| EtAc | 29.4221 | 0.0048 | 56.7224 |
| iPrAc | 70.5157 | 99.9531 | 43.2007 |
| nPrAc | 0.0077 | 0.0177 | 0.0003 |
| impurities | 0.0027 | 0.0026 | 0.0028 |
| HAC | 0.0021 | 0.0036 | 0.0010 |
| | 100.0000 | 100.0000 | 100.0000 |
| Ratios | | | |
| Residue/Feed | K/K | | 0.49 |
| Reflux/Distillate | K/K | | 3.4 |
| Top Temperature | ° C. | | 82.7 |
| Base Temperature | ° C. | | 90.1 |

Example 2

TABLE 5

Reactor Column. Conditions and Results

| | RUN | A | B |
|---|---|---|---|
| Coproduction of Ethyl Acetate and isoPropyl Acetate | | | |
| Feed | % ETOH | 57.5 | 10.2 |
| | % IPA | 40.66 | 89.8 |
| | % H2O | 0.018 | 0.0 |
| Organic Phase (OVHD Decanter) | % HAC | 0.0 | 0.0 |
| | % H2O | 3.39 | 1.89 |
| | % ETOH | 0.75 | 0.06 |
| | % IPA | 2.08 | 2.05 |
| | % nPROH | 0.0 | 0.0 |
| | % ETAC | 64.92 | 11.66 |
| | % iPRAC | 28.86 | 79.57 |
| | % nPRAC | 0.0 | 0.0 |
| Aqueous Phase (OVHD Decanter) | % HAC | 0.0 | 0.0 |
| | % H2O | 85.7 | 88.35 |
| | % ETOH | 2.61 | 0.25 |
| | % IPA | 3.75 | 4.95 |
| | % nPROH | 0.0 | 0.0 |
| | % ETAC | 6.89 | 1.54 |
| | % iPRAC | 1.05 | 3.12 |
| | % nPRAC | 0.0 | 0.0 |
| Liq. Ph. Catalyzed Reaction Zone | % HAC | 81.19 | 80.59 |
| | % H2O | 1.74 | 2.4 |
| | % ETOH | 0.18 | 0.0 |
| | % IPA | 0.7 | 0.75 |
| | % nPROH | 0.0 | 0.0 |
| | % ETAC | 9.88 | 1.29 |
| | % iPRAC | 6.32 | 13.6 |
| | % nPRAC | 0.0 | 0.0 |
| Main Ratios | | | |
| Reflux/HOAc Feed | K/K | 4.02 | 4.02 |
| Reflux/Distillate | K/K | 1.16 | 1.57 |
| Wash Water/Distillate | K/K | 0.225 | 0.219 |
| Wash Water/HOAc Feed | K/K | 0.784 | 0.77 |
| Recycled Esters/HOAc Feed | K/K | 1.438 | 0.45 |
| Crude EtAc/Crude iPrAc | K/K | 2.25 | 0.15 |
| Base Temperature | ° C. | 107 | 109 |
| Top temperature | ° C. | 74 | 78 |
| Decanter Temperature | ° C. | 5 | 5 |

What we claim is:

1. A process for the simultaneous coproduction and recovery of ethyl acetate and isopropyl acetate, comprising the steps of:
   (a) reacting a stream comprising ethanol and isopropyl alcohol with acetic acid, in the liquid phase, in the presence of an acidic catalyst wherein the reaction is carried out in a reactor column at an elevated temperature and pressure sufficient to effect esterification of the ethanol and isopropyl alcohol to form a mixture of ethyl acetate and isopropyl acetate;
   (b) removing the mixture of ethyl acetate and isopropyl acetate from the reactor column as an overhead stream;
   (c) condensing the overhead stream to form a liquid reaction product mixture;
   (d) separating the liquid reaction product mixture into an organic phase comprising ethyl acetate and isopropyl acetate and an aqueous phase comprising primarily water;
   (e) directing the organic phase to a first distillation column and removing a stream comprising ethyl acetate and isopropyl acetate from the first distillation column;
   (f) directing the stream from the first distillation column to a second distillation column and removing an ethyl acetate product stream from the top of the second distillation column and a steam comprising isopropyl acetate from the bottom of the second distillation column; and
   (g) directing the stream comprising isopropyl acetate to a third distillation column and removing an isopropyl acetate product stream from the bottom of the third distillation column.

2. The process of claim 1 wherein the stream comprising ethanol and isopropyl alcohol is subjected to azeotropic distillation to produce a purified stream comprised of ethanol and isopropyl alcohol and comprising less than 300 ppm of an alcohol having a boiling point greater than the boiling point of isopropyl alcohol.

3. The process of claim 2 wherein the stream comprising ethanol and isopropyl alcohol is derived from a Fischer Tropsch alcohol mixture.

4. The process of claim 1 wherein the stream comprising ethanol and isopropyl alcohol is a Fischer Tropsch alcohol mixture and the stream is not purified prior to use.

5. The process of claim 4 wherein esters other than ethyl acetate and isopropyl acetate are produced in the reactor column and are separated form ethyl acetate and isopropyl acetate during recovery of ethyl acetate and isopropyl acetate.

6. The process of claim 5 wherein the stream comprising ethanol and isopropyl alcohol comprises from about 10% to about 90% ethanol and from about 10% to about 90% isopropyl alcohol.

7. The process of claim 5 wherein the stream comprising ethanol and isopropyl alcohol comprises from about 60% to about 80% ethanol and from about 20% to about 40% isopropyl alcohol.

8. The process of claim 4 wherein each of the ethyl acetate and the isopropyl acetate is recovered at greater than about 99.5% purity.

9. The process of 4 wherein each of the ethyl acetate and the isopropyl acetate is recovered at a purity of greater than 99.7%.

* * * * *